(12) United States Patent
Auner et al.

(10) Patent No.: US 11,375,897 B2
(45) Date of Patent: Jul. 5, 2022

(54) SYSTEM AND METHOD FOR CHARACTERIZATION OF A BRAIN TISSUE SAMPLE USING RAMAN MARKER REGIONS

(71) Applicants: HENRY FORD HEALTH SYSTEM, Detroit, MI (US); WAYNE STATE UNIVERSITY, Detroit, MI (US)

(72) Inventors: Gregory William Auner, Livonia, MI (US); Michelle Brusatori, Sterling Heights, MI (US); Steven N. Kalkanis, Bloomfield Hills, MI (US); Lisa Scarpace, Dearborn, MI (US)

(73) Assignees: Henry Ford Health System, Detroit, MI (US); Wayne State University, Detroit, MI (US)

( * ) Notice: Subject to any disclaimer, the term of this patent is extended or adjusted under 35 U.S.C. 154(b) by 179 days.

(21) Appl. No.: 16/605,926

(22) PCT Filed: Apr. 20, 2018

(86) PCT No.: PCT/US2018/028628
§ 371 (c)(1),
(2) Date: Oct. 17, 2019

(87) PCT Pub. No.: WO2018/195466
PCT Pub. Date: Oct. 25, 2018

(65) Prior Publication Data
US 2020/0138293 A1 May 7, 2020

Related U.S. Application Data

(60) Provisional application No. 62/487,679, filed on Apr. 20, 2017.

(51) Int. Cl.
*A61B 5/00* (2006.01)

(52) U.S. Cl.
CPC .......... *A61B 5/0042* (2013.01); *A61B 5/0075* (2013.01); *A61B 5/0084* (2013.01)

(58) Field of Classification Search
CPC .................................................. A61B 5/0042
See application file for complete search history.

(56) References Cited

U.S. PATENT DOCUMENTS

| 5,579,773 A | 12/1996 | Vo-Dinh et al. |
| 5,615,673 A | 4/1997 | Berger et al. |

(Continued)

FOREIGN PATENT DOCUMENTS

| WO | 2015-060590 | * | 1/2015 | .......... A61B 5/0075 |
| WO | 2015006716 A1 | | 1/2015 | |

OTHER PUBLICATIONS

International Search Report and Written Opinion for Application No. PCT/US2018/028628, dated Jul. 20, 2018, 14 pages.

(Continued)

*Primary Examiner* — Joseph M Santos Rodriguez
(74) *Attorney, Agent, or Firm* — Brooks Kushman P.C.

(57) ABSTRACT

A system for characterization of a brain tissue sample includes a laser having an excitation fiber and a probe coupled to the excitation fiber for irradiating the brain tissue sample with light at an excitation wavelength. The probe further includes a plurality of return fibers for receiving light scattered from the brain tissue sample, wherein each return fiber includes a microfilter that permits light to pass for a different, spaced apart marker region. A Raman spectrometer is in communication with the plurality of return fibers, and a processor is in communication with the Raman spectrometer for analyzing Raman spectra within the marker regions to identify a tissue type of the brain tissue sample as one of (Continued)

normal white matter brain tissue, normal grey matter brain tissue, brain tumor tissue, infiltrating tumor tissue, and necrotic tissue.

17 Claims, 2 Drawing Sheets

(56) References Cited

U.S. PATENT DOCUMENTS

| | | | |
|---|---|---|---|
| 2003/0191398 A1 | 10/2003 | Motz et al. | |
| 2004/0263843 A1 | 12/2004 | Knopp et al. | |
| 2006/0139633 A1 | 6/2006 | Puppels et al. | |
| 2008/0221457 A1 | 9/2008 | Zeng et al. | |
| 2009/0066934 A1 | 3/2009 | Gao et al. | |
| 2012/0184827 A1 | 7/2012 | Shwartz et al. | |
| 2012/0259229 A1 | 10/2012 | Wang et al. | |
| 2012/0328178 A1 | 12/2012 | Remiszewski et al. | |
| 2013/0137944 A1 | 5/2013 | Jeong et al. | |
| 2013/0238251 A1 | 9/2013 | Zhu et al. | |
| 2014/0125977 A1 | 5/2014 | Volodin et al. | |
| 2016/0139051 A1* | 5/2016 | Auner | A61B 5/14546 356/301 |
| 2017/0020460 A1 | 1/2017 | Leblond et al. | |

OTHER PUBLICATIONS

International Preliminary Report on Patentability for Application No. PCT/US2018/028628, dated Oct. 31, 2019, 10 pages.

Extended European Search Report for Application No. 14822531.1, dated Jan. 26, 2017, 8 pages.

International Search Report and Written Opinion for Application No. PCT/US2014/046391, dated Nov. 18, 2014, 12 pages.

Beljebbar et al., "Ex vivo and in vivo diagnosis of C6 glioblastoma development by Raman spectroscopy coupled to a microprobe", Analytical and Bioanalytical Chemistry, vol. 398, Issue 1, pp. 477-487, first online Jun. 26, 2010.

Kalkanis et al., "Raman spectroscopy to distinguish grey matter, necrosis, and glioblastoma multiforme in frozen tissue sections", J. Neurooncol, 2014, pp. 477-485.

Kirsch et al., "Raman spectroscopic imaging for an vivo detection of cerebral brain metastases", Anal Bioanal Chem, 2010, pp. 1701-1713.

Amharref et al., "Discriminating healthy from tumor and necrosis tissue in rat brain tissue samples by Raman spectral imaging", Biochimica et Biophysica Acta 1768, 2007, pp. 2605-2615.

Auner et al., "Conclusions and data analysis: a 6-year study of Raman spectroscopy of solid tumors at a major pediatric institute", Pediatr. Surg. Int., 2013, pp. 129-140.

Beljebbar et al., "Ex vivo and in vivo diagnosis of C6 glioblastoma development by Raman spectroscopy coupled to a microprobe", Anal Bioanal Chem, 2010, pp. 477-487.

Dingari et al., "Wavelength selection-based nonlinear calibration for transcutaneous blood glucose sensing using Raman spectroscopy", Journal of Biomedical Optics, vol. 16(8), Aug. 5, 2011, pp. 087009-1-087009-10.

\* cited by examiner

SYSTEM AND METHOD FOR CHARACTERIZATION OF A BRAIN TISSUE SAMPLE USING RAMAN MARKER REGIONS

CROSS-REFERENCE TO RELATED APPLICATIONS

This application is the U.S. national phase of PCT Application No. PCT/US2018/028628 filed Apr. 20, 2018, which claims the benefit of U.S. provisional application Ser. No. 62/487,679 filed Apr. 20, 2017, the disclosures of which are hereby incorporated in their entirety by reference herein.

TECHNICAL FIELD

Embodiments relate to a system and method for characterization of a brain tissue sample using Raman spectra marker regions.

BACKGROUND

The estimated incidence of new primary brain and central nervous system (CNS) tumors for 2016 is 77,670, with 16,616 predicted deaths resulting from malignant tumors (Central Brain Tumor Registry of the United States. (2015). 2015 *CBTRUS Fact Sheet*. Retrieved from http://www.cbtrus.org/factsheet/factsheet.html). Glioblastoma (GBM), an extremely aggressive primary brain tumor with an average life expectancy of approximately 12-18 months, accounts for 15.4% of all tumors (Tumor Board Review, Second Edition:Guideline and Case Reviews in Oncology). Surgical excision, which provides a means of diagnosis and cytoreduction, is one of the most effective treatments for such tumors. Growing literature support demonstrates early maximal resection, while preserving a patient's functional status, is critical for optimal patient outcome (Jakola A S et al. (2012); JAMA 308:1881-1888). This suggests a need for new technologies aimed at achieving maximal safe resections.

Many tools have been developed to aid the neurosurgeon with intraoperative tumor identification and delineation. Image guided surgical techniques include intra-operative MRI (iMRI), fluorescence guided surgery, neuronavigation and ultrasonography. Neuronavigation systems, based on preoperative imaging, allow the surgeon to reference and correlate an image domain to the operative field. However, such techniques are severely limited by brain shift, which is problematic for margin assessment. Intra-operative MRI helps to correct for brain shift, as images are created during surgery with a portable or nearby device. Although more accurate information is obtained than with preoperative imaging, "results" are viewed and interpreted after image acquisition as opposed to real time tissue interrogation. Intraoperative ultrasound provides real time imaging to accommodate for brain shift; however, such systems tend to be less sensitive to tumor margins and accuracy compared to MRI (Selbekk, T et al. (2013); Acta Neurochir 155:973-980). 5-ALA fluorescence-guided surgery provides real time visualization of the operating field and allows areas of high-grade transformation to be viewed; however, confusion between normally fluorescing tissue and tumor can cause resection beyond the area of fluorescence (Stummer W et al. (2011); J Neurosurg 114:613-623) and a tight blood-brain barrier may minimize fluorescence (Li Y et al. (2014); World Neurosurg 82:175-185).

SUMMARY

In one embodiment, a system for characterization of a brain tissue sample includes a laser having an excitation fiber and a probe coupled to the excitation fiber for irradiating the brain tissue sample with light at an excitation wavelength. The probe further includes a plurality of return fibers for receiving light scattered from the brain tissue sample, wherein each return fiber includes a microfilter that permits light to pass for a different, spaced apart marker region. A Raman spectrometer is in communication with the plurality of return fibers, and a processor is in communication with the Raman spectrometer for analyzing Raman spectra within the marker regions to identify a tissue type of the brain tissue sample as one of normal white matter brain tissue, normal grey matter brain tissue, brain tumor tissue, infiltrating tumor tissue, and necrotic tissue.

The processor may analyze at least three marker regions between 0 cm$^{-1}$ and 1800 cm$^{-1}$ to identify the tissue type of the brain tissue sample. The spaced apart marker regions may include 400-600 cm$^{-1}$, 690-720 cm$^{-1}$, 850-950 cm$^{-1}$, 990-1020 cm$^{-1}$, 1050-1100 cm$^{-1}$, 1130-1200 cm$^{-1}$, 1260-1365 cm$^{-1}$, 1400-1480 cm$^{-1}$, 1500-1530 cm$^{-1}$, and 1570-1700 cm$^{-1}$ to distinguish the tissue type of the brain tissue sample. The processor may analyze at least one peak within a marker region between 2840 cm$^{-1}$ and 2950 cm$^{-1}$ to identify the tissue type of the brain tissue sample, wherein the at least one peak may be at 2853.1 cm$^{-1}$.

The processor may analyze a peak height, a peak shape, a peak area, or a peak slope of Raman spectra within the marker region to characterize the tissue type of the brain tissue sample. The processor may analyze a ratio of peak heights of Raman spectra between different marker regions to characterize the tissue type of the brain tissue sample.

In another embodiment, a system for characterization of a brain tissue sample includes a laser having an excitation fiber and a probe coupled to the excitation fiber for irradiating the brain tissue sample with light at an excitation wavelength. The probe further includes a plurality of return fibers for receiving light scattered from the brain tissue sample, wherein each return fiber includes a microfilter that permits light to pass for a different, spaced apart marker region between 0 cm$^{-1}$ and 1800 cm$^{-1}$. A Raman spectrometer is in communication with the plurality of return fibers, and a processor is in communication with the Raman spectrometer for analyzing Raman spectra within the marker regions, wherein the processor analyzes at least three marker regions to identify the tissue type of the brain tissue sample.

The marker regions may include 400-600 cm$^{-1}$, 690-720 cm$^{-1}$, 850-950 cm$^{-1}$, 990-1020 cm$^{-1}$, 1050-1100 cm$^{-1}$, 1130-1200 cm$^{-1}$, 1260-1365 cm$^{-1}$, 1400-1480 cm$^{-1}$, 1500-1530 cm$^{-1}$, and 1570-1700 cm$^{-1}$ to distinguish the tissue type of the brain tissue sample, and the processor may identify the brain tissue sample as one of normal white matter brain tissue, normal grey matter brain tissue, brain tumor tissue, infiltrating tumor tissue, and necrotic tissue.

In another embodiment, a method for characterization of a brain tissue sample includes providing a laser having an excitation fiber, a probe coupled to the excitation fiber and further including a plurality of return fibers which each include a microfilter that permits light to pass for a different, spaced apart marker region, a Raman spectrometer in communication with the plurality of return fibers, and a processor in communication with the Raman spectrometer. The method further includes irradiating the brain tissue sample with light at an excitation wavelength, receiving light scattered from the brain tissue sample, analyzing Raman spectra within the marker regions, and identifying a tissue type of the brain tissue sample as one of normal white matter brain tissue, normal grey matter brain tissue, brain tumor tissue, infiltrating tumor tissue, and necrotic tissue.

The method may include analyzing at least three marker regions between 0 cm$^{-1}$ and 1800 cm$^{-1}$ to identify the tissue type of the brain tissue sample. The spaced apart marker regions may include 400-600 cm$^{-1}$, 690-720 cm$^{-1}$, 850-950 cm$^{-1}$, 990-1020 cm$^{-1}$, 1050-1100 cm$^{-1}$, 1130-1200 cm$^{-1}$, 1260-1365 cm$^{-1}$, 1400-1480 cm$^{-1}$, 1500-1530 cm$^{-1}$, and 1570-1700 cm$^{-1}$ to distinguish the tissue type of the brain tissue sample. The method may include analyzing at least one peak within a marker region between 2840 cm$^{-1}$ and 2950 cm$^{-1}$ to identify the tissue type of the brain tissue sample, wherein the at least one peak may be at 2853.1 cm$^{-1}$. The method may include analyzing at least one of a peak height, a peak shape, a peak area, a peak slope, or a ratio of peak heights to characterize the tissue type of the brain tissue sample. The tissue type of the brain tissue sample may be identified real time in vivo.

DETAILED DESCRIPTION

Figure 1:
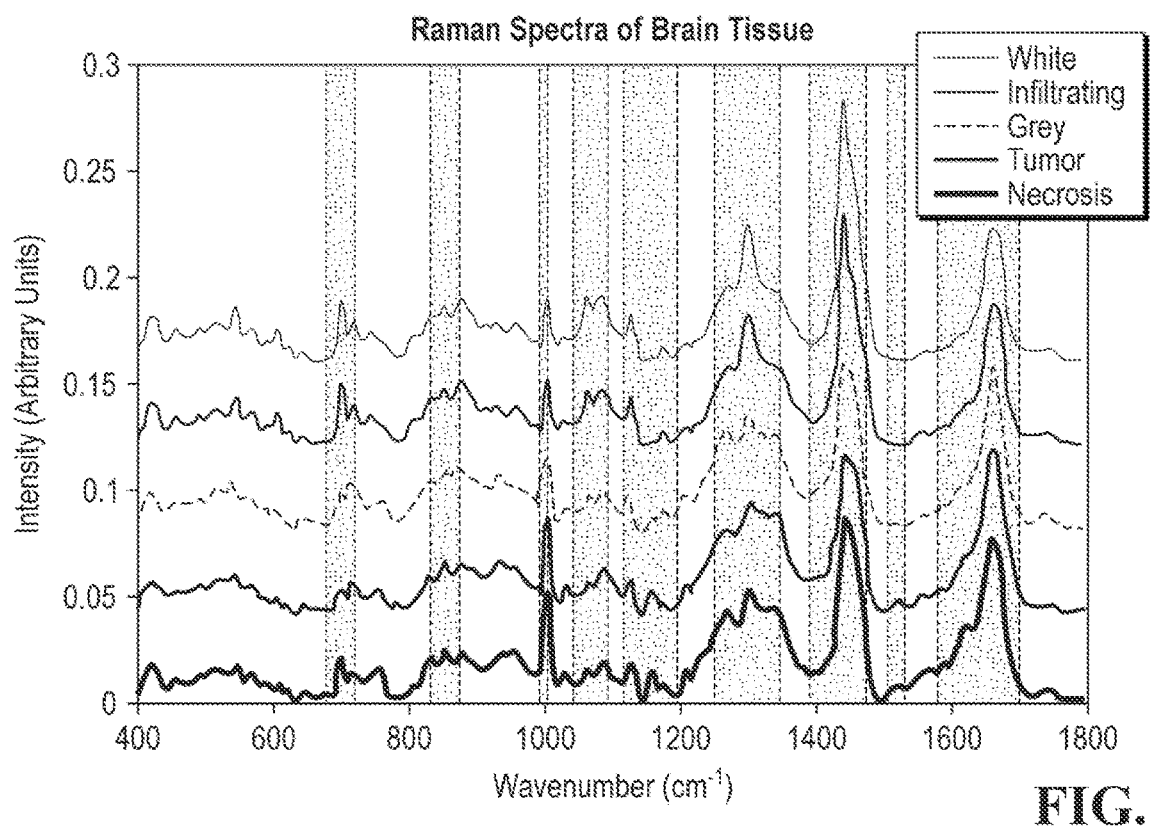
FIG. 1 is a graph of mean Raman spectra of intraoperative samples in the spectral region of 400-1800 cm$^{-1}$ classified as 100% normal (white matter, grey matter), 100% tumor, 100% infiltrating, or necrosis, wherein these traces are ordered from top to bottom.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Raman spectroscopy is a non-contact, non-destructive optical technique with demonstrated ability to detect changes in the chemical composition and/or molecular structure between diseased and healthy tissue. This technique has the potential to overcome the limitation of current methodologies for intraoperative evaluation of tissue and can be utilized in conjunction with imaging modalities such as MRI and ultrasound for more in-depth characterization of residual tumor. This real-time platform can accommodate for brain shift and may provide molecular information necessary for intraoperative margin assessment. Intraoperative histology based on microscopy is still the most accepted approach to determine tumor margins. However, this 'gold standard' method can take up to 30 min for results. New techniques that offer accurate, rapid, pathology results are highly desirable and can lead to better patient outcome as well as reduce time and cost associated with tumor resections.

The translation of Raman spectroscopy for clinical use involves the development of in vivo instrumentation aimed at achieving high sensitivity while reducing the size and cost. Embodiments disclosed herein include a portable Raman spectroscopy apparatus and methods for ex vivo, in vitro and in vivo analysis and characterization of brain tissue.

In Raman spectroscopy, a sample is irradiated with a specific wavelength of light, typically from a laser. The majority of light is scattered from the sample at the same frequency (wavelength) as the incident radiation (laser). This is known as Rayleigh (or elastic) scattering. However, a small fraction of light (~1 in 10$^7$ photons) is inelastically scattered at optical frequencies that differ from the incident radiation. The inelastic scattering of photons is termed the Raman Effect and is due to changes in molecular polarizability during vibration which provide chemical and structural information uniquely characteristic of the tissue under study.

According to an embodiment, a Raman spectroscopic study was performed on fresh excised brain tissue to distinguish between normal tissue, tissue with infiltrating tumor cells, dense tumor tissue, and necrotic tissue. Although demonstrated on excised tissue, the system and markers disclosed herein are suited for intraoperative use. From the unique tissue-specific, spectroscopic profiles, several key Raman bands were identified and used to build fundamental statistical models to delineate tissue type.

In the study, 118 Raman spectra from 28 tissue samples from 8 patients, immediately following surgical resection, were recorded with a Raman apparatus equipped with a 1200 l/mm grating, a 576×400 pixel thermoelectric-cooled charge-coupled device (CCD), and a 300 mW 785 nm laser as the excitation source. Laser light was focused onto the sample, and spectra were acquired using 57 mW at the sample over a spectral range of 100-3200 cm$^{-1}$ with 1 accumulation at an integration time of 10 seconds. Two to eight distinct regions were measured on each tissue sample. Following spectral acquisition, the specimens were submitted to pathology for evaluation.

Raman spectra were subsequently pre-processed over a spectral range of 400 to 1800 cm$^{-1}$ and 2500-3200 cm$^{-1}$ to minimize any fluorescence contributions and to provide better interpretability and higher robustness for subsequent classification. Spectral pre-processing included: (1) spike elimination to remove cosmic rays, (2) a 17-point Savitzky-Golay filter to reduce random noise, (3) background subtraction via a 5$^{th}$ order polynomial fit to remove spectral contributions due to fluorescence and (4) normalized.

In one embodiment, classification may be accomplished by the following method: pre-processed spectra can be grouped into separate databases based on pathologic findings and analyzed using discriminant function analysis, DFA (IBM SPSS Statistics). Linear discriminant analysis (LDA) is a multivariate technique that builds a predictive model for group membership. For an "N" group analysis, the model is composed of "N-1" functions which are linear combinations of predictor variables whose coefficients maximize separation between predefined groups. Though mathematically different, each discriminant function differentiates a case into a group, where the first function provides the most discriminating power between groups, the second provides second most, and so on (Acevedo, M F (2012) *Data Analysis and Statistics for Geography, Environmental Science, and Engineering*. Boca Raton, Fla. CRC Press). In the case of DF analysis of Raman spectral data, discriminant functions are generated using intensity values at particular wavenumbers. Based upon the DF scores, a sample is classified into a group:

$$DF_{km} = a_0 + a_1 I_{1km} + a_2 I_{2km} + \ldots + a_p I_{pkm} \qquad [1]$$

where $DF_{km}$ is the score of the discriminant function for case m in $k^{th}$ group, where $k=1 \ldots N-1$. $I_{jkm}$ is the Raman intensity at the corresponding wavenumber $\gamma$ for case m in group k, and $a_j$ is the function. For accuracy confirmation, cross validation is done based on the "leave-one-out" principle. Key assumptions of LDA are: 1) the variables are independent, 2) the independent variables follow a multivariate normal distribution, 3) different classes are described by identical covariance matrices, 4) multivariate outliers are absent, and 5) there is an absence of multicollinearity. It has been suggested that discriminant analysis is relatively robust to slight violations of these assumptions (Lachenbruch, Pa. (1975); *Discriminant analysis*, NY: Hafner).

The "leave-one out" method works by removing one spectrum from the original matrix and performing a DFA analysis on the remaining observations (spectra). The omitted spectrum is then classified. The process is repeated until each spectrum has been evaluated. Discriminant function analysis allows for rapid, accurate identification of neural tissue without loss of meaningful biologic data.

An alternative method is the use of an artificial intelligence program (AI) or deep learning algorithm. The neural network may employ two layers of Convolution Neural Networks (CNN) followed by a Partially Connected Neural Network (PCNN). A CNN aims at generating a feature from local information of each band. It takes the tensor $\gamma$ (rearranged tensor from preprocessed data z) as an input and convolutes the $\xi$-axis of $\gamma$ with a set of kernels. The kernel size for first layer is 2 and for the second layer is w−1. As a result, the output shape of the CNN becomes $N t \times N \Psi \times \kappa 2 \times 1$. The PCNN, following CNNs, connects the generated features of bands associated with a corresponding macromolecule. A uodontogenic method is used for reduction of the connections as the input-output relationship is known for this case. The output of this layer will be in the shape of $N t \times N \Phi$ and it is connected to a logistic regression classifier with two outputs as identified and altered. The training objective is to minimize the number of errors on unseen samples (zero-one lose). The log-likelihood of the classifier is maximized since the zero-one lose is not differentiable. Alternatively, it is possible to minimize the negative log-likelihood (NLL). The stochastic gradient decent method was used to update the parameters of the network, and training took tens of thousands of epochs until it reached the optimal point. However, the validation score and cost was calculated in the end of an epoch and the best or most early cost was considered as the optimal one. The model was tested by feeding the testing database to the network and further analyses were performed to evaluate the model.

Figure 2:
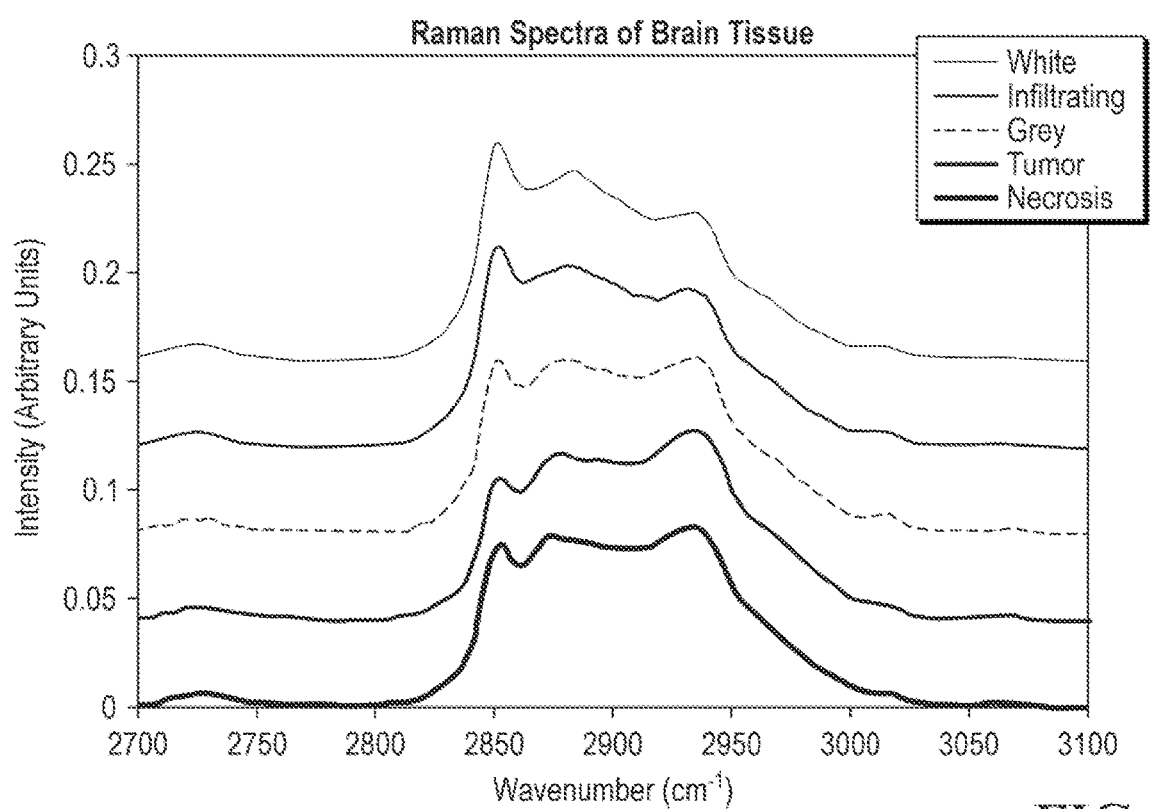
FIG. 2 is a graph of mean Raman spectra of intraoperative samples in the spectral region of 2700-3100 cm$^{-1}$ classified as 100% normal (white matter, grey matter), 100% tumor, 100% infiltrating, or necrosis, wherein these traces are ordered from top to bottom.

The mean Raman spectra of surgically resected samples deemed as 100% normal tissue, 100% tumor tissue, 100% infiltrating tissue, or necrotic tissue are plotted as relative Raman intensity versus wavenumber or Raman shift (FIG. 1 and FIG. 2, respectively). It is evident from the plots that the mean spectra of each of the pathological conditions is distinct with spectral differences arising from changes in nucleic acid, protein, lipid and carbohydrate content that occur with disease progression.

Recreating the isolated Raman bands spanning 400-600 $cm^{-1}$, 690-720 $cm^{-1}$, 850-950 $cm^{-1}$, 990-1020 $cm^{-1}$, 1050-1100 $cm^{-1}$, 1130-1200 $cm^{-1}$, 1260-1365 $cm^{-1}$, 1400-1480 $cm^{-1}$, 1500-1530 $cm^{-1}$, 1570-1700 $cm^{-1}$ (shaded regions bounded by broken lines in FIGS. 1 and 2) shows differences that may be used to characterize the tissue. The peak location, relative height (corresponding to intensity in that region) and shape of the bands provide discrete identification. This may be achieved by identifying sub regions identifying points along each of the identified Raman regions at the Nyquist limit or greater which will provide a recreation of the spectral marker region. This allows for elimination of other regions that may confound the analysis and simplifies the device requirements. This may be analyzed by, but not limited to, DFA, PCA, vector machine or machine learning algorithms.

According to the disclosed embodiments, Raman spectra in the range of 0 $cm^{-1}$ to 1800 $cm^{-1}$ include the following marker regions for identification of brain tumor, infiltrating tumor, normal brain tissue, and necrotic tissue: Raman bands spanning 400-600 $cm^{-1}$, 690-720 $cm^{-1}$, 850-950 $cm^{-1}$, 990-1020 $cm^{-1}$, 1050-1100 $cm^{-1}$, 1130-1200 $cm^{-1}$, 1260-1365 $cm^{-1}$, 1400-1480 $cm^{-1}$, 1500-1530 $cm^{-1}$, 1570-1700 $cm^{-1}$ show differences that may be used to characterize the tissue. In one embodiment, at least three separate marker regions in the range of 0 $cm^{-1}$ to 1800 $cm^{-1}$ can be used to identify the tissue type of a brain tissue sample.

Raman spectra in the range of 2500 $cm^{-1}$ to 3200 $cm^{-1}$ correspond to CH, $CH_2$, and $CH_3$ stretching vibrations which differentiate brain tumor, infiltrating tumor, normal brain tissue, and necrotic tissue. According to the disclosed embodiments, tissue differentiation may be obtained in this range by peak height and location, by differentiating the area under the peaks, by the slope of the peaks, by shift in the peaks, by the slope in the peak heights, or by single wavelength measurements using band pass filters for each peak. Identification of brain tumor tissue, infiltrating tumor tissue, normal brain tissue, and necrotic tissue may also be obtained in the range of 1800 $cm^{-1}$ to 3200 $cm^{-1}$ by a series of three or more discrete notch filters used as the Nyquist limit (3 points) for recreating a Gaussian fit to the marker peaks, by the height of the 2853.1 peak, by the ratios of the specific peaks outlined above to each other one by one, or by the ratio of the peaks in the range of 1800 $cm^{-1}$ to 3200 $cm^{-1}$. In one embodiment, at least one peak within a marker region between 2840 $cm^{-1}$ to 2950 $cm^{-1}$ can be used to identify the tissue type of a brain tissue sample. In non-limiting examples, a slope of at least three peaks within the marker region of 2840 $cm^{-1}$ to 2950 $cm^{-1}$ could be used, or a peak at 2853.1 $cm^{-1}$ could be used to identify the tissue type of the brain tissue sample.

Figure 3:
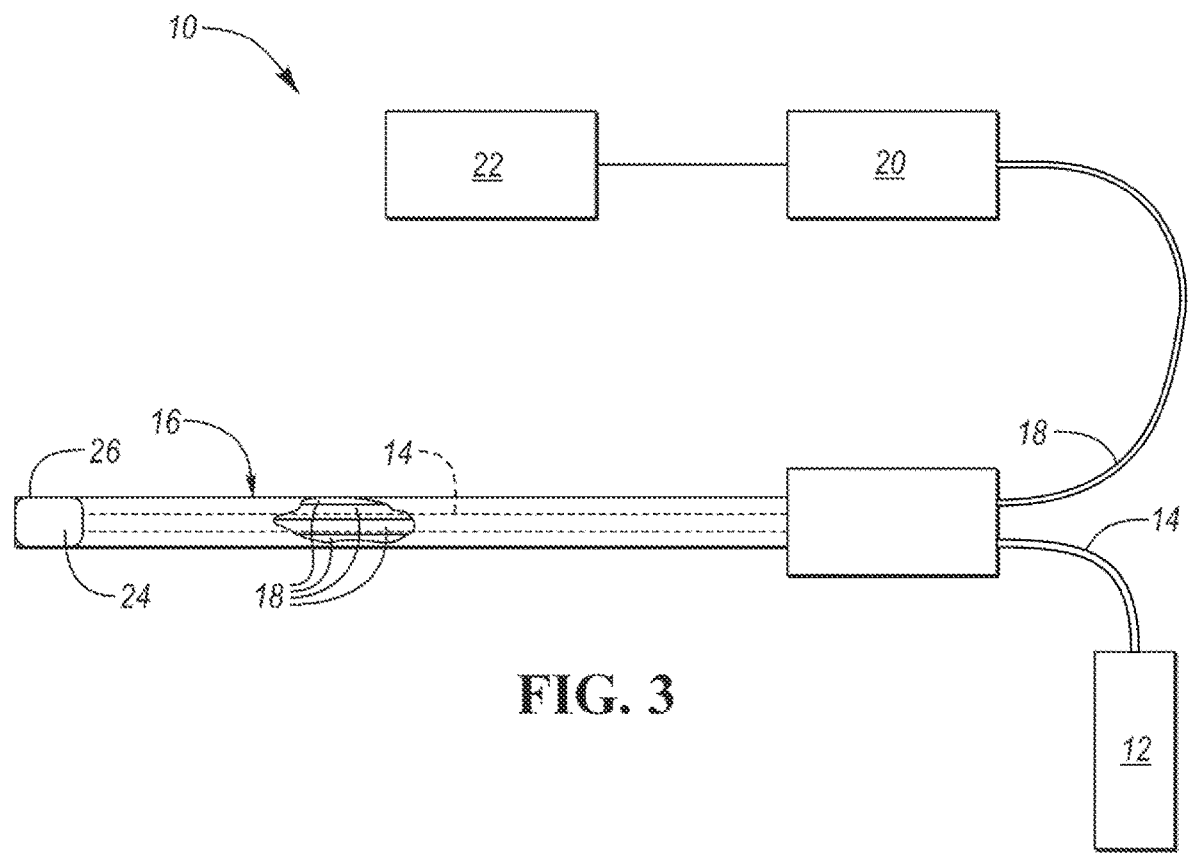
FIG. 3 illustrates a system for characterizing a brain tissue sample according to an embodiment.

With reference to FIG. 3, a system 10 for characterization of a brain tissue sample is illustrated. The system 10 includes a laser 12 having an excitation fiber 14 and a probe 16 coupled to the excitation fiber 14 for irradiating the brain tissue sample with light at an excitation wavelength. The probe 16 further includes a plurality of return fibers 18 for receiving light scattered from the brain tissue sample, wherein each return fiber 18 includes a microfilter that permits light to pass for a different, spaced apart marker region. A Raman spectrometer 20 is in communication with the plurality of return fibers 18, and a processor 22 is in communication with the Raman spectrometer 20 for analyzing Raman spectra within the marker regions to identify a tissue type of the brain tissue sample as one of normal white matter brain tissue, normal grey matter brain tissue, brain tumor tissue, infiltrating tumor tissue, and necrotic tissue.

The marker regions may include 400-600 $cm^{-1}$, 690-720 $cm^{-1}$, 850-950 $cm^{-1}$, 990-1020 $cm^{-1}$, 1050-1100 $cm^{-1}$, 1130-1200 cm$^{-1}$, 1260-1365 cm$^{-1}$, 1400-1480 cm$^{-1}$, 1500-1530 cm$^{-1}$, and 1570-1700 cm$^{-1}$ to distinguish the tissue type of the brain tissue sample. The processor 22 may analyze a peak height of Raman spectra within the marker region to characterize the tissue type of the brain tissue sample, where the marker region may include 2853.1 cm$^{-1}$. The processor 22 may alternatively analyze at least one of a peak shape, a peak area, or a peak slope of Raman spectra within the marker region to characterize the tissue type of the brain tissue sample. Still further, the processor 22 may analyze a ratio of peak heights of Raman spectra between different marker regions to characterize the tissue type of the brain tissue sample.

Figure 4:
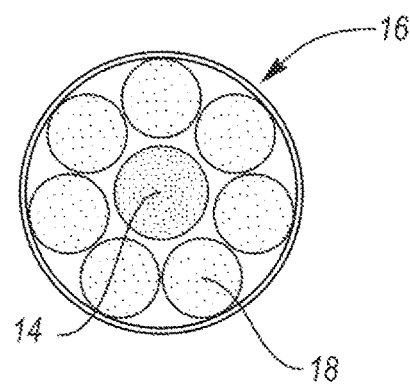
FIG. 4 illustrates a cross-sectional view of a probe according to an embodiment.

Each return fiber 18 may include a blocking filter that blocks light at the excitation wavelength. As shown in FIG. 4, the excitation fiber 14 may be centrally located within the probe 16 and the return fibers 18 may peripherally surround the excitation fiber 16. Alternatively, the excitation fiber 18 may surround the return fibers 18. The probe 16 may include a lens 24 on a distal end 26 thereof.

As shown in FIGS. 3 and 4, a probe 16 to a spectrometer 20 is provided that spans, for example, either 0 cm$^{-1}$ to 1800 cm$^{-1}$, 1800 cm$^{-1}$ to 3200 cm$^{-1}$, or 0 cm$^{-1}$ to 3200 cm$^{-1}$. The probe 16 may be a tracking probe, and may include discrete, integrated microfilters to pass through light recreating the identification spectral regions or optical absorbers that eliminate unwanted regions. The disclosed system may provide a tone variation depending on spectral measurements. The probe 16 may include an inner laser (or monochromatic light) optical fiber 14, beam path or waveguide, and an outside return optical fiber bundle 18. At one end 26 thereof, the probe 16 may include a sealed optical spherical lens 24. An excitation beam 14 to the sample may be centrally disposed, and return fibers 18 may be peripherally disposed within the probe, where the probe 16 may have a diameter, in a non-limiting example, of approximately 3 mm. The return fibers 18 may have an excitation wavelength blocking filter, and may have specific notch microfilters for marker wavelengths.

Standard screening for neoplastic processes typically involves gross inspection and multiple biopsies of aberrant tissue. Raman spectroscopy can assist in uncovering the molecular basis of disease and provide objective, quantifiable molecular information for diagnosis and treatment evaluation. Embodiments disclosed herein provide a real-time characterization platform and the disclosed technology does not require tagging or genetic primers. The system and method can provide significant benefit to an array of other surgical resections including pancreatic, breast, bone, and prostate cancers as well as real-time identification of infections including antibiotic resistant species. Furthermore, the technology can be translated to a clinical setting.

Non- or minimally invasive in-vivo tools that can provide rapid tissue assessment, and/or monitor treatment therapies have potential application in many fields of medicine. Raman spectroscopy can assist in uncovering the molecular basis of disease and provide objective, quantifiable molecular information for diagnosis and treatment evaluation. This may complement or possibly supplant current methods of surgical guidance in tumor resection. The prospect of near real-time imaging combined with accuracy in characterizing malignancies and distinguishing them from normal brain tissue and tissue with infiltrating cancer cells will be a revolutionary step forward in how physicians practice medicine.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for characterization of a brain tissue sample, the system comprising:
   a laser having an excitation fiber;
   a probe coupled to the excitation fiber for irradiating the brain tissue sample with light at an excitation wavelength, the probe further including a plurality of return fibers for receiving light scattered from the brain tissue sample, wherein each return fiber includes a microfilter that permits light to pass for a different, spaced apart spectral marker region;
   a Raman spectrometer in communication with the plurality of return fibers; and
   a processor in communication with the Raman spectrometer for analyzing Raman spectra in a range of 2500 cm$^{-1}$ to 3200 cm$^{-1}$ to differentiate a tissue type of the brain tissue sample between white matter brain tissue, grey matter brain tissue, brain tumor tissue, infiltrating tumor tissue, and necrotic tissue.

2. The system of claim 1, wherein the processor analyzes at least one peak within a spectral marker region between 2840 cm$^{-1}$ to 2950 cm$^{-1}$ to identify the tissue type of the brain tissue sample.

3. The system of claim 2, wherein the at least one peak is at 2853.1 cm$^{-1}$.

4. The system of claim 1, wherein the processor analyzes a peak height of Raman spectra within the spectral marker region to characterize the tissue type of the brain tissue sample.

5. The system of claim 1, wherein the processor analyzes a peak shape of Raman spectra within the spectral marker region to characterize the tissue type of the brain tissue sample.

6. The system of claim 1, wherein the processor analyzes a peak area of Raman spectra within the spectral marker region to characterize the tissue type of the brain tissue sample.

7. The system of claim 1, wherein the processor analyzes a peak slope of Raman spectra within the spectral marker region to characterize the tissue type of the brain tissue sample.

8. The system of claim 1, wherein the processor analyzes a ratio of peak heights of Raman spectra between different spectral marker regions to characterize the tissue type of the brain tissue sample.

9. A method for characterization of a brain tissue sample, the method comprising:
   providing a laser having an excitation fiber, a probe coupled to the excitation fiber and further including a plurality of return fibers which each include a microfilter that permits light to pass for a different, spaced apart spectral marker region, a Raman spectrometer in communication with the plurality of return fibers, and a processor in communication with the Raman spectrometer;
   irradiating the brain tissue sample with light at an excitation wavelength;
   receiving light scattered from the brain tissue sample;
   analyzing Raman spectra in a range of 2500 cm$^{-1}$ to 3200 cm$^{-1}$; and identifying a tissue type of the brain tissue sample as one of white matter brain tissue, grey matter brain tissue, brain tumor tissue, infiltrating tumor tissue, and necrotic tissue.

10. The method of claim 9, wherein analyzing Raman spectra includes analyzing at least one peak within a spectral marker region between 2840 $cm^{-1}$ to 2950 $cm^{-1}$ to identify the tissue type of the brain tissue sample.

11. The method of claim 10, wherein the at least one peak is at 2853.1 $cm^{-1}$.

12. The method of claim 9, wherein analyzing Raman spectra within the spectral marker regions includes analyzing a peak height, to characterize the tissue type of the brain tissue sample.

13. The method of claim 9, wherein the tissue type of the brain tissue sample is identified real time in vivo.

14. The method of claim 9, wherein analyzing Raman spectra within the spectral marker regions includes analyzing a peak shape to characterize the tissue type of the brain tissue sample.

15. The method of claim 9, wherein analyzing Raman spectra within the spectral marker regions includes analyzing a peak area to characterize the tissue type of the brain tissue sample.

16. The method of claim 9, wherein analyzing Raman spectra within the spectral marker regions includes analyzing a peak slope to characterize the tissue type of the brain tissue sample.

17. The method of claim 9, wherein analyzing Raman spectra within the spectral marker regions includes analyzing a ratio of peak heights to characterize the tissue type of the brain tissue sample.

* * * * *